United States Patent [19]

Kamienski

[11] Patent Number: 4,555,498

[45] Date of Patent: Nov. 26, 1985

[54] PREPARATION OF CERTAIN ALKALINE EARTH METAL ORGANOMETALLIC COMPOUNDS

[75] Inventor: Conrad W. Kamienski, Gastonia, N.C.

[73] Assignee: Lithium Corporation of America, Gastonia, N.C.

[21] Appl. No.: 669,675

[22] Filed: Nov. 8, 1984

Related U.S. Application Data

[63] Continuation-in-part of Ser. No. 551,917, Nov. 15, 1983, abandoned.

[51] Int. Cl.$^4$ .............................. C08F 4/48; C08F 4/50; C07C 31/30
[52] U.S. Cl. .................................. 502/153; 502/154; 502/171; 568/851
[58] Field of Search ...................... 502/154, 153, 171; 568/851

[56] References Cited

U.S. PATENT DOCUMENTS

| | | | |
|---|---|---|---|
| 3,541,149 | 11/1970 | Langer | 568/851 X |
| 3,903,019 | 9/1975 | Hargis et al. | 502/154 |
| 4,033,900 | 7/1977 | Hargis et al. | 502/154 |
| 4,092,268 | 5/1978 | Zarauz | 502/154 X |
| 4,260,519 | 4/1981 | Aggarwal et al. | 502/154 |
| 4,297,240 | 10/1981 | Bingham et al. | 502/153 |

*Primary Examiner*—Patrick P. Garvin
*Attorney, Agent, or Firm*—Sidney Wallenstein; Harry V. Strampel; Ralph R. Rath

[57] ABSTRACT

Stable, hydrocarbon-soluble organobarium-, organocalcium-, and organostrontium-containing polymerization initiators are prepared by reacting certain calcium, barium or strontium alkoxides with organolithium, diorganomagnesium or triorganoaluminum compounds and combinations thereof. By way of illustration, the barium alkoxides soluble in hydrocarbon or chlorinated hydrocarbon solvents are prepared by reacting a suspension of barium amide in a hydrocarbon or a chlorinated hydrocarbon solvent with stoichiometric quantities of certain alcohols, alone or in the presence of chelating tertiary di- or polyamines. Alcohols suitable for the preparation of hydrocarbon- or chlorinated hydrocarbon-soluble barium alkoxides are $C_4$–$C_{12}$ aliphatic and cycloaliphatic alcohols possessing alkyl branches at the one or two-positions, or mixtures of such alcohols. Other suitable alcohols are 2-alkoxy-1-alkanols and $\gamma$-alkoxy-poly(ethyleneoxy)-1-ethanols.

30 Claims, No Drawings

PREPARATION OF CERTAIN ALKALINE EARTH
METAL ORGANOMETALLIC COMPOUNDS

CROSS-REFERENCE TO RELATED APPLICATION

The present application is a continuation-in-part of application Ser. No. 551,917, filed Nov. 15, 1983 and now abandoned.

BACKGROUND OF THE INVENTION

This invention relates to certain organometallic compounds and the preparation thereof and, more specifically, is directed to certain novel organobarium, organocalcium and organostrontium compounds and processes for making such compounds.

It has heretofore been known that certain barium alkoxides in conjunction with alkyllithium or dialkylmagnesium compounds promote the polymerization and copolymerization of, for example, 1,3-butadiene to a polymer having a high trans-1,4 microstructure and possessing unique beneficial properties in its use as a tire rubber.

It has also heretofore been known that the barium or calcium compounds, particularly for the foregoing purposes, must be present as an alkoxide and that, generally, the barium or calcium alkoxide interacts strongly with the alkyllithium or dialkylmagnesium compounds to form complexes of, presumably, alkylbarium or alkylcalcium alkoxides with the alkyllithium or dialkylmagnesium compounds.

For maximum efficiency in this interchange reaction and for use as a polymerization initiator, it is particularly advantageous to employ barium alkoxides which possess a high solubility in liquid hydrocarbon media. Initial experimental work was done utilizing barium tert-butoxide (A. Onishi et al, U.S. Pat. No. 3,629,213, Dec. 21, 1971). However, barium tert-butoxide, by itself, was found to possess a low order of solubility in liquid aliphatic hydrocarbon solvents (U.S. Pat. No. 4,044,900, July 5, 1977); while barium ethoxide is even less soluble (Z. M. Baydakova, et al (a) *High Molecular Wt. Compounds* 1976 Vol. (A) XVIII, No. 9 (Russian) (b) Vysokomol.Soedin. Series B 1977, 19 (10) 767–70 (Russian). Later, others (U.S. Pat. No. 4,355,156) have shown that barium tert-butoxide, in conjunction with barium tert-decanolate and barium hydroxide, has a superior solubility in toluene over barium tert-butoxide-barium hydroxide alone (I. G. Hargis, R. A. Livigni and S. L. Aggarwal, ACS Symposium Series, 1982, No. 193 (Elastomers Rubber Elasticity).

Barium or calcium alkoxides are generally prepared by reacting a solution of barium or calcium metal in liquid ammonia or methylamine, with the desired alcohol, followed by evaporation of the solvent and subsequent drying in vacuo. Solutions of the barium or calcium alkoxides are then made up in the desired hydrocarbon solvent.

It is one of the objects of my invention to make available barium, calcium and strontium alkoxides possessing a particularly high solubility in liquid hydrocarbon solvents, and in the hydrocarbon solutions thereof.

It is another object of my invention to provide a simplified process for the preparation of such barium calcium and strontium alkoxides directly in the hydrocarbon solvents.

Another object of my invention is to provide a novel method of preparing barium, calcium and strontium amides.

A still further object of my invention is to provide a process for the preparation of liquid hydrocarbon-soluble stable complexes of alkylbarium, alkylcalcium and alkylstrontium alkoxides with alkyllithium, dialkylmagnesium with or without trialkylaluminum compounds using, advantageously, barium, calcium or strontium alkoxide solutions.

SUMMARY OF THE INVENTION

In accordance with my invention, certain alcohols are reacted with barium, calcium or strontium amides in liquid aliphatic or aromatic hydrocarbon solvent media to form highly soluble, stable solutions of barium alkoxides, calcium alkoxides and strontium alkoxides.

Whereas, in the aforementioned U.S. Pat. No. 4,355,156, barium tert-alkoxides were found to possess a high solubility in hydrocarbon solvents, in my hands this was not the case. For example, the solubility of barium tert-butoxide in toluene was found by me to be only 0.37M at ambient temperature; that of barium tert-amylate, 0.23M in toluene; and that of barium 3-methyl-3-pentanolate, only 0.08M in cyclohexane. In addition, the stability of these solutions deteriorated with time (precipitation of product within a few days).

On the other hand, I have found that although, for example, linear barium primary alkoxides possess little or no solubility in hydrocarbon solvents, those with 2-alkyl substituents in the alcohol moiety of said alkoxides possess a much higher solubility, especially in the presence of an equimolar quantity of chelating tertiary di- or polyamine, especially advantageously N,N,N',N'-tetramethylethylenediamine (hereafter in the specification referred to as TMEDA), although such additions are optional in various cases. The following table gives solubility data for some typical barium alkoxides of this series:

| Barium Alkoxide | Solvent | Conc (M) | Equimolar TMEDA |
|---|---|---|---|
| 2-Ethyl-1-butoxide | Toluene | 0.55 | + |
| 2-Methyl-1-pentyloxide | Cyclohexane | 0.63 | + |
| 2-Ethyl-1-hexyloxide | Cyclohexane | 0.66 | − |
| 2-Ethyl-4 methyl-1-pentyloxide | Cyclo hexane | 0.75 | − |

Additional alcohols which form hydrocarbon-soluble barium and calcium salts are those belonging to the classes of (a) 2-alkoxy-1-alkanols, ROCH$_2$CH(R')OH, and (b) $\gamma$-alkoxy-poly(ethylenoxy)-1-ethanols, RO(CH$_2$CH$_2$O)$_n$CH$_2$CH$_2$OH (R is C$_1$–C$_{12}$ hydrocarbyl and R' is hydrogen or C$_1$–C$_3$ hydrocarbyl), such as 2-methoxy-1-ethanol, 2-butoxy-1-ethanol, 2-butoxy-1-methyl-1-ethanol, 2-hexyloxy-1-ethanol, and the like, commonly referred to in the art as "Cellosolve" solvents (Union Carbide Corp.). In the case of the aforesaid $\gamma$-alkoxy poly(ethyleneoxy)-1-ethanols, R is a C$_1$–C$_{12}$ hydrocarbyl group, but most desirably ethyl, n-butyl and n-hexyl, and n may vary from 0 to 4. One can also employ mixtures of these alcohols with each other and the monohydric alcohols described above in the proportions given therein. In the case of the aforesaid γ-alkoxy poly(ethyleneoxy)-1-ethanols, R is a $C_1$–$C_{12}$ hydrocarbyl group, but most desirably ethyl, n-butyl and n-hexyl, and n may vary from 0 to 4. One can also employ mixtures of these alcohols with each other and the monohydric alcohols described above in the proportions given therein.

In one method of the practice of my invention, barium or calcium amide is suspended in the liquid hydrocarbon solvent of choice; and a slightly less than stoichiometric quantity of 2-alkyl substituted $C_4$–$C_{12}$ normal monohydric alcohol, or mixtures thereof with $C_3$–$C_{12}$ secondary monohydric alcohol in which the OH group is attached to the second carbon atom, alone or in solution in a liquid hydrocarbon solvent, are added to the stirred barium amide or calcium amide suspension. Ammonia is rapidly evolved; and the mixture is heated to the boiling point for such period of time (commonly several hours) necessary to be certain that all ammonia is gone from the solution.

TMEDA, or equivalent agents, may be added during the reaction as a complexing agent, as required, to promote solubility, especially in the case of the lower molecular weight ($C_4$ and $C_5$) 2-alkyl-substituted alkoxides.

The resulting barium or calcium alkoxide solutions may be filtered to remove unreacted barium or calcium amide and other solid impurities, or may be used directly in organometallic complexes preparations.

The organometallic complexes of my invention, it will be seen, are prepared by admixture of $C_2$–$C_{18}$, more advantageously $C_4$–$C_8$, alkyllithium, dialkylmagnesium and/or trialkylaluminum compounds with the barium (or calcium) alkoxide solutions of my invention and, in certain cases, as will be seen, with complexing solubilizers, such as tertiary amines, where not previously added to said metal alkoxides. Clear solutions result which are stable over a considerable period of time (commonly several weeks or more).

The reactions involved in regard to the preparation of the following illustrative composition according to my invention are shown in the following steps:

Step 1
Reaction of Barium Amide with 2-Methylpentanol:

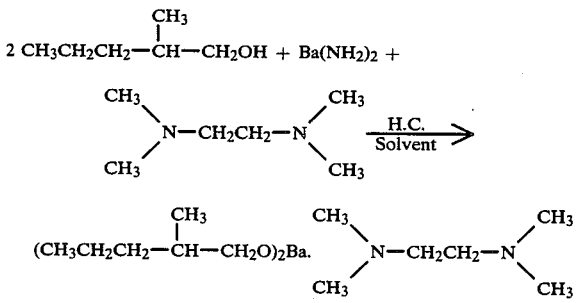

Step 2
Reaction of Step 1 Product with Dibutylmagnesium:

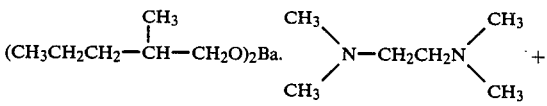

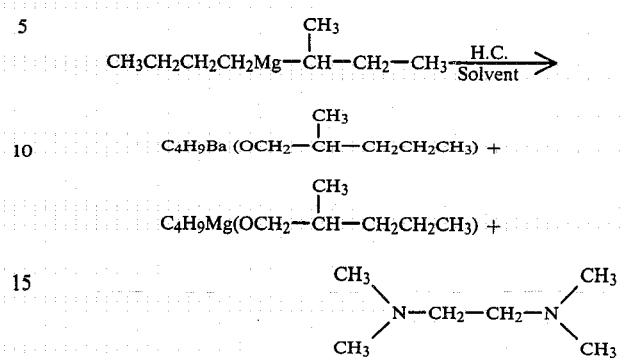

2-Alkyl-substituted monohydric primary or normal alcohols ($C_4$–$C_{12}$), which are reacted with barium, calcium or strontium amides in various of the embodiments of my invention, are exemplified by isobutyl alcohol, 2-methyl-1-pentanol, 2-ethyl-1-butanol, 2-ethyl-1-pentanol, 2-ethyl-1-hexanol, 2-ethyl-4-methyl-1-pentanol, 2-propyl-1-heptanol, 2-methyl-1-hexanol, 2-ethyl-5-methyl-1-octanol, and the like, or mixtures thereof. Preferred 2-alkyl substituted monohydric normal alcohols are 2-methyl-1-pentanol and 2-ethyl-1-hexanol.

$C_3$–$C_{12}$ secondary monohydric alcohols in which the OH group is attached to the second carbon atom, which, in admixture with the aforesaid 2-alkyl-substituted monohydric normal $C_4$–$C_{12}$ alcohols in the reaction with the aforesaid alkaline earth metal amides, is another of the embodiments of my invention. Such $C_3$–$C_{12}$ secondary monohydric alcohols are exemplified by isopropyl alcohol, secondary butyl alcohol, 4-methyl-2-pentanol, 2-pentanol, 2-hexanol, 5-methyl-2-hexanol, 4,6-dimethyl-2-heptanol, and the like, and mixtures thereof. Cycloaliphatic alcohols, exemplified by cyclohexanol and cyclopentanol, are also included as examples of secondary alcohols which can be used in admixture with said 2-alkyl-substituted $C_4$–$C_{12}$ monohydric primary or normal alcohols.

The "CELLOSOLVE" and the "CARBITOL" alkanols have been referred to above, together with illustrative examples thereof and, therefore, require no repetition.

The barium amide, calcium amide and strontium amide can be produced by any convenient means, but are obviously obtained in a finely divided form.

One novel method, which is particularly useful, involves dissolution of barium metal in liquid ammonia, followed by addition of an aromatic solvent, such as toluene. This addition converts the dissolved barium metal to a slurry of barium amide, which can be filtered and dried, or the ammonia evaporated off, residual ammonia being removed by subsequent heating of the slurry to the boiling point of the aromatic solvent. A finely-divided slurry of barium amide in the aromatic solvent is obtained which can be used directly in the preparation of barium alkoxides.

The reaction of the aforesaid amides, particularly desirably barium amide, with the aforesaid alcohols to produce the desired hydrocarbon-soluble barium alkoxides can be carried out at any convenient temperature. Preferably, the reaction is carried out at room temperature; and the reaction mixture is then heated to reflux for a period of time (usually 1 to 4 hours) to complete the removal of by-product ammonia.

In certain cases, the addition of a complexing tertiary amine, such as TMEDA, is required to promote solution.

It is understood that, although barium and calcium amides are preferred precursors to the metal alkoxides of my invention, there can be employed other barium- or calcium-containing precursors such as barium or calcium metal itself and/or barium or calcium organo-metallics such as, for example, phenylcalcium iodide, phenylbarium iodide, isopropylcalcium bromide, isopropylcalcium chloride, dimethylcalcium, diethylbarium, dibenzylbarium, and the like.

In those instances where the alcohols of my invention are 2-alkoxy-1-alkanols or γ-alkoxy-poly(ethyleneoxy)-1-ethanols, lower $C_1$–$C_{13}$ barium and calcium alkoxides such as calcium ethoxide may be used in place of the respective metals or metal amides. The resulting products are lower $C_1$–$C_3$ alcohol solvates of the calcium and barium 2-alkoxy-1-alkoxides, show the structure $M(OCH_2CH(R')OR_2.(R''OH)_x$, or calcium and barium γ-alkoxy-poly(ethyleneoxy)-1-ethoxides, $M(OCH_2OCH_2CH_2)_nOR)_2.(R'OH)_x$ where x=zero to 2.

The solution of barium or other heretofore-stated metal alkoxide is next reacted with the organometal of choice, as shown in the aforementioned equation (Step 2 above), in the presence of a complexing tertiary amine, where needed, if such amine has not already been premixed with said metal alkoxide. There is generally no particularly superior order of admixing these reagents, except that good agitation be maintained throughout said admixture. For example, the aforesaid metal alkoxide may be added to the organometal, or vice versa. Generally, addition of one reagent to the other is carried out incrementally (i.e., not all at once) so as to maintain good contact of the reagents throughout. Also, it has been found to be advantageous to cool the reaction during said admixture, keeping the temperature generally below room temperature, and more preferably near 0°.

Various organometal reagents may be admixed with the aforesaid metal alkoxides of this invention. Within the scope of my invention are organolithium compounds generally soluble in hydrocarbon media, such as ethyllithium, isopropyllithium, n-hexyllithium, n-octyllithium and mixtures of these, such as n-butyllithium and ethyllithium, which form soluble products in hydrocarbon solvents.

In place of, or in admixture with, the organolithium compounds, one may employ diorganomagnesium compounds soluble in hydrocarbon media for reaction with the barium, calcium or strontium alkoxides of my invention. Examples of these diorganomagnesium compounds, are diethylmagnesium, n-butylethyl magnesium, diisopropylmagnesium, n-butyl-sec-butylmagnesium, n-butyl-n-octylmagnesium, di-n-hexylmagnesium, di-sec-butylmagnesium, di-2-methylbutylmagnesium and di-n-octylmagnesium and the like, and mixtures thereof.

In admixture with the alkyllithium, dialkylmagnesium or mixtures thereof, there may be included triorganoaluminum compounds normally soluble in hydrocarbon media, such as triisobutylaluminum (TIBAL), triethylaluminum, tri-n-butylaluminum, tri-n-hexylaluminum and tri-n-octylaluminum and the like, and mixtures thereof.

In regard to the complexing solubilizer for the aforesaid alkaline earth metal alkoxides, or admixture therewith of the aforesaid organometal reagents, said reagents being disclosed in the above four immediately-preceding paragraphs hereof. While TMEDA is especially satisfactory for use in the practice of the present invention, other aliphatic tertiary amines can be utilized, among which may be mentioned azaoxa-alkanes, aza-alkyloxacycloalkanes or oxa-alkylazacycloalkanes of the formulas:

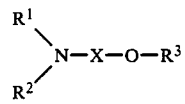

I

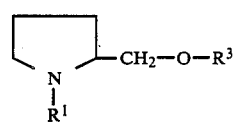

II

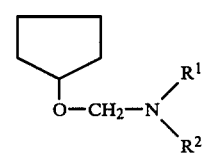

III

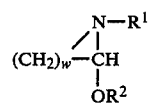

IV

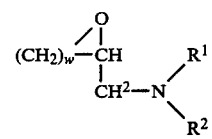

V where $R^1$, $R^2$ and $R^3$ are the same or different alkyls, each containing from 1 to 4 carbon atoms, namely, methyl, ethyl, n-propyl, isopropyl, n-butyl, isobutyl and t-butyl; X is a non-reactive group, such as

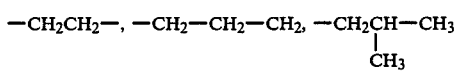

or other divalent aliphatic hydrocarbon or alkylene radical, preferably containing from 2 to 4 carbon atoms; and w is 1 to 4. Illustrative examples include, for instance, 2-dimethylaminoethylmethyl ether [$(CH_3)_2N$—$CH_2$—$CH_2$—$OCH_3$], 2-diethylaminoethylmethyl ether [$(C_2H_5)_2N$—$CH_2$—$CH_2$—$OCH_3$], and 2-dimethylaminopropylmethyl ether [$(CH_3)_2N$—$CH_2$—$CH_2$—$CH_2$—$OCH_3$].

TMEDA and generally functionally-equivalent aliphatic tertiary amines are disclosed in U.S. Pat. No. 3,451,988. Such aliphatic tertiary amines, as there disclosed, include, among others, those which are represented by the formulas:

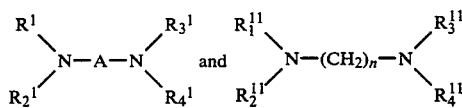

wherein $R^1$, $R_2^1$, $R_3^1$ and $R_4^1$ are the same or different alkyl radicals of 1 to 5 carbon atoms, inclusive; A is a non-reactive group; $R_1^{11}$, $R_2^{11}$, $R_3^{11}$ and $R_4^{11}$ are the same or different alkyl radicals of 1 to 3 carbon atoms, inclusive; and n is an integer between 1 and 4, inclusive. The disclosure of said aliphatic tertiary amines in said patent is incorporated herein by reference.

The hydrocarbon solvents useful in my invention may be any normally liquid aliphatic, cycloaliphatic or aromatic compounds, such as pentane, hexane, heptane, cyclopentane, cyclohexane, benzene and toluene, and the like, and mixtures thereof. The particularly preferred solvent is cyclohexane.

The following Examples show illustrative runs carried out in accordance with my invention. It will, of course, be understood that many other stable organometallic compositions can be made pursuant to my invention, utilizing different ones of the aforesaid alkaline earth metal alkoxides; different complex-forming solubilizers (other than TMEDA); different organometallics than the particular alkyllithiums, dialkylmagnesiums or trialkylaluminums given in the Examples; different liquid hydrocarbon solvents; and different reaction temperatures, etc., without departing from the guiding principles and teachings disclosed herein. All temperatures recited are in degrees Centigrade.

EXAMPLE I

Preparation of a Hydrocarbon-Soluble Complex of Barium 2-Ethylhexyloxide and Dibutylmagnesium (DBM)

A. Preparation of Barium Amide

Into 200 ml of liquid ammonia at $-60°$ is added, slowly, 50 g (0.365 g at.) of barium metal (broken crowns). After stirring for about 1 hour, 50 ml of toluene is added slowly below $-50°$. Within 30 minutes, evidence of reaction is noted, the reddish-bronze color of the metal-ammonia solution changing to green and then to yellow. The mixture is stirred at $-50°$ to $-60°$ for 1 hour longer and then allowed to warm up, ammonia slowly being driven off overnight.

To the flask containing a slurry of yellow solids is added 50 ml of toluene; the mixture is heated and stirred to distill off toluene. About 50 ml of toluene is distilled off, after which no further odor of ammonia is noted. The mixture is cooled, filtered, washed with pentane twice, and blown dry under an argon stream. The product is transferred to 125 ml Wheaton bottles in a glove bag. Total recovered product=59.34 g (0.35 moles, 96%). Found for Ba: 80.1 wt.%; Theory—81.1%.

B. Preparation of Barium-2-Ethyl-1-Hexyloxide (Hexanolate)

13.4 g (0.0791 moles) of $Ba(NH_2)_2$ is suspended in 100 ml of cyclohexane and mechanically stirred while neat 2-ethylhexanol (20.5 g, 24.7 ml, 0.158 moles) is added slowly, via syringe. All of the solid reacts and goes into solution. The mixture is heated to boiling for about 4 to 5 hours to remove $NH_3$; cooled; filtered; and analyzed for barium. Several analyses are run, resulting in an average molarity value of 0.65M. The total volume of clear, light amber filtrate is about 110 ml. Yield of recovered Ba in solution=0.0715 moles (90%). PMR of the alkoxide solution shows alkoxide protons ($OCH_2$) at 5.0$\delta$ relative to the cyclohexane protons as 2.85$\delta$.

C. Preparation of a Hydrocarbon-Soluble Complex of Barium 2-Ethylhexyloxide and DBM To 20 ml of a 0.57M solution of barium 2-ethylhexyloxide in cyclohexane, there is added at room temperature all at once 7.3 ml of 1.56M dibutylmagnesium (DBM) in cyclohexane. Heat is generated, the temperature rising to about 40°; and a deep amber color develops immediately, gradually darkening to a red-brown. The solution stays clear throughout. No significant shift of alpha-methylene alkoxide protons is noted in proton NMR.

ANALYTICAL TECHNIQUES

Barium, magnesium, lithium and aluminum are assayed in the presence of each other in the following Examples. Aluminum is determined complexometrically by addition of an excess of either EDTA or CDTA at pH 5 to 6 and back titration of the excess with standard $Zn^{++}$ solution to a colored end point. Magnesium is determined by precipitation of the Al as $Al(OH)_3$, and Ba as $BaSO_4$, followed by complexometric titration with EDTA at pH 10; while barium is determined by subtracting the Mg value obtained from a separate determination of both Mg and Ba via back titration of an excess of EDTA with $Zn^{++}$.

EXAMPLE II

Preparation of a Hydrocarbon-Soluble Complex of Barium 2-Methyl-Pentyloxide, TMEDA, Butylethylmagnesium (DBME) and TIBAL

A. Preparation of Barium 2-Methyl-1-Pentyloxide (Pentanolate)

In a similar manner to part B of EXAMPLE I above, 12.47 g, 15.1 ml (0.122 moles) of 2-methyl-2-pentanol are added gradually to a stirred slurry of 10.34 g (0.061 moles) of barium amide in 55 ml of cyclohexane. Severe thickening of the reaction mixture occurs after addition of the first 6 ml of the alcohol, resulting in a foaming problem. In order to allow completion of the reaction, 8.5 ml (0.056 moles) of TMEDA is added to the mixture. The addition of TMEDA causes the mixture to become quite fluid, thus allowing the completion of the alcohol addition. After stirring for a further period of about 1 hour, an additional 1 ml of TMEDA is added (total TMEDA present—0.063 moles); and the mixture is heated overnight in an oil bath at about 80° (just below reflux point of the solution). No discernable solids are present. The mixture is then heated to a full reflux to drive off dissolved ammonia; cooled; filtered; and analyzed for barium;
Found: Ba—0.83 Molar
Total volume=85 ml
Recovered: Ba=0.054 Moles
Yield—88%

B. Preparation of a Hydrocarbon-Soluble Complex of Barium 2-Methyl-Pentyloxide-TMEDA, Butylethylmagnesium (DBME) and TIBAL To 4.8 ml of 1.31M butylethylmagnesium[a] (DBME) in heptane is added 9.2 ml of cyclohexane, followed by 10 ml of a 0.63M solution of barium 2-methyl-pentyloxide-TMEDA complex in cyclohexane with cooling at 0°. A sticky second phase appears on the walls, which dissolves on addition of 7.6 ml of 0.92M TIBAL in heptane. A slightly hazy light amber solution results. Analysis of a sample of the clear solution shows essentially all of the ions in solution:
Initial: Ba—6.30 mmoles, Mg—6.29 mmoles, Al—6.99 mmoles.
Found: Ba—6.13 mmoles, Mg—7.14 mmoles, Al—7.14 mmoles.

(a) butyl—1:1 mixture of n-and sec-butyl; butyl:ethyl ratio=3

EXAMPLE III

Preparation of a Hydrocarbon-Soluble Complex of Barium 2-Ethyl-Hexyloxide, n-Butyllithium and TIBAL to 9.6 ml of 0.65M barium 2-ethylhexyloxide solution in cyclohexane (plus an additional 11.6 ml of cyclohexane), there is added 3.4 ml of 1.92M n-butyllithium in cyclohexane to give a clear, dark amber solution. Addition of 7.8 ml of 0.92M TIBAL in heptane does not change the appearance of the solution. Analysis of the clear solution for ions shows essentially complete recovery of ions.
Initial: Ba—6.2 mmoles, Li—6.5 mmoles, Al—7.2 mmoles
Found: Ba—5.8 mmoles, Li—6.6 mmoles, Al—7.1 mmoles

EXAMPLE IV

Preparation of a Hydrocarbon-Soluble Complex of Barium 2-Ethylhexyloxide, Butyloctylmagnesium and TIBAL To 7.6 ml of a 0.86M solution of butyloctylmagnesium (Bu/Oct=3) in heptane, diluted with an equal volume of cyclohexane, there is added 10 ml of a 0.65M solution of barium 2-ethylhexyloxide in cyclohexane while cooling at 0°. A somewhat hazy solution results, which clears up on heating to about 35°-40°. Next, addition of 7.8 ml of a 0.92M solution of TIBAL in heptane results in a clear, light amber solution. Analysis for Ba, Mg and Al in the solution shows all of these ions to be present in essentially the amounts originally added:
Initial: Ba—6.50 mmoles, Mg—6.54 mmoles, Al—7.18 mmoles
Found: Ba—6.17 mmoles, Mg—6.95 mmoles, Al—7.35 mmoles

EXAMPLE V

Preparation of a Hydrocarbon-Soluble Complex of Barium 2-Methylpentyloxide (Pentanolate).TMEDA with Di-Normal-Hexylmagnesium (DNHM) and TIBAL To 17.5 ml of a 0.36M di-normal-hexylmagnesium solution in heptane, there is added 10 ml of 0.63M barium 2-methylpentyloxide.TMEDA solution in cyclohexane with cooling at 0°. A light hazing is noted. Next, a volume of 7.6 ml of 0.92M TIBAL is added, and the mixture is allowed to stand overnight. A clear yellow-amber solution results. Analysis shows that this solution contains 6.81 mmoles of Al (Theory=6.99), 6.95 mmoles of Mg (Theory=6.30), and 5.90 mmoles of Ba (Theory=6.30).

EXAMPLE VI

Preparation of a Hydrocarbon-Soluble Complex of the Mixed Salt, Barium 2-Ethylhexlyoxide/4-Methyl-2-Pentyloxide, with Dibutylmagnesium (DBM) and TIBAL To 7.8 ml of 0.92M TIBAL solution in heptane, diluted with 10 ml of cyclohexane, there is added a mixture of 5 ml of 0.65M barium 2-ethylhexyloxide and 5 ml of 0.83M barium 4-methyl-2-pentyloxide dissolved in cyclohexane while shaking and cooling. A very slight haze develops on adding the alkoxide mix. The same is apparent on addition of 4.75 ml of 1.56M dibutylmagnesium in cyclohexane to this mixture. No TMEDA is added. The solution clears up on warming to 30°-35°. A clear, light amber solution results. The solution is analyzed for Ba, Al and Mg ions.
Theory: Ba—7.4 mmoles, Al—6.5 mmoles, Mg—7.6 mmoles
Found: Ba—7.0 mmoles, Al—6.7 mmoles, Mg—8.3 mmoles

EXAMPLE VII

Preparation of a Hydrocarbon-Soluble Complex of Calcium 2-Ethylhexyloxide and DBM A. Preparation of Calcum Amide In a manner essentially the same as that described in part A of EXAMPLE I for the preparation of barium amide, there is prepared 50 g of calcium amide.

B. Preparation of Calcium 2-Ethylhexyloxide

To 7.2 g (0.1 mole) of calcium amide slurried in 100 ml of cyclohexane, there is added 23.5 g (28.2 ml, 0.18 moles) of 2-ethyl-1-hexanol gradually over a 10-15 minute period. Ammonia is given off throughout the addition. The mixture is heated to reflux for several hours to remove entrained ammonia, and is then cooled and filtered. The resultant clear, light amber solution is 0.8M in Ca.

C. Reaction of Calcium 2-Ethylhexyloxide with DBM

To 10 ml of 0.8M calcium 2-ethylhexyloxide in cyclohexane, there is added 5.1 ml of 1.56M DBM in cyclohexane over a 15-minute period. A light amber, clear solution results.

EXAMPLE VIII

Preparation of Hydrocarbon-Soluble Calcium 2-Ethoxy-1-Ethoxide

To 8.02 g (0.2 gram-moles) in the form of pellets suspended in 175 ml cyclohexane and 45 ml of toluene is added a crystal of iodine and the mixture heated to reflux. A solution of 40 ml (0.4 moles) of 2-ethoxyethanol in an equal volume of cyclohexane is added over a 1-hour period. The mixture becomes a grey fluid suspension and is further refluxed and stirred for an additional 12 hours. After cooling and filtration, 140 mls of a light amber-colored solution is obtained, which is 0.77 Molar in calcium (53%).

EXAMPLE IX

Preparation of Hydrocarbon-Soluble Barium 2-Ethoxy-1-Ethoxide 10.8 g (0.0638 moles) of barium amide is suspended in 60 ml toluene. To the stirred amide slurry, there is slowly added 10.92 g (11.73 ml) (0.121 moles) of 2-ethoxyethanol, the by-product ammonia being vented off as formed. After addition of the alcohol is complete, the mixture is gradually heated to reflux. After heating at reflux for several hours, the exhaust gases no longer contain ammonia, and the mixture is cooled to room temperature under argon. The mixture is filtered to remove excess barium amide and the filtrate, 65 ml, is found to be 0.81 Molar in barium (yield=88%).

EXAMPLE X

Preparation of Hydrocarbon-Soluble Calcium 2-Ethoxy-1-Ethoxide

To 26 g (0.2 moles) of calcium ethoxide, suspended in 200 ml of toluene, there is added, all at once, 36 grams (39 ml, 0.40 moles) of 2-ethoxyethanol. The mixture is slowly heated to 50° for 1 hour and then heated for another 4 hours at 50°. The resulting mixture is cooled and filtered and the filtrate is found to be 0.83 Molar in calcium.

I claim:

1. In a process for the preparation of hydrocarbon or chlorinated hydrocarbon-solvent solutions of calcium, barium and strontium alkoxides, the steps which comprise providing a suspension of a member of the group of metals or amides of calcium, barium, strontium or dialkylmetallic compounds thereof in a volatile liquid hydrocarbon or chlorinated hydrocarbon solvent and then reacting said suspension with an alcohol as such or in a solution in a volatile liquid hydrocarbon or chlorinated hydrocarbon, said alcohol being selected from the group of (a) aliphatic 2-alkyl substituted $C_4$–$C_{12}$ monohydric primary alcohols, and (b) mixtures of said (a) alcohols with $C_3$–$C_{12}$ aliphatic secondary monohydric alcohols in which the hydroxyl group is attached to the second carbon atom, and removing such ammonia as forms during the reaction.

2. The process of claim 1, in which the amide is barium amide.

3. The process of claim 2, in which the (a) alcohol is at least one member selected from the group of isobutyl alcohol, 2-methyl-1-pentanol, 2-ethyl-1-butanol, 2-ethyl-1-pentanol, 2-ethyl-1-hexanol, 2-ethyl-4-methyl-1-pentanol, 2-propyl-1-heptanol, 2-methyl-1-hexanol and 2-ethyl-5-methyl-1-octanol.

4. The process of claim 1, in which the (b) alcohol is at least one member selected from the group of isopropyl alcohol, secondary butyl alcohol, 4-methyl-2-pentanol, 2-pentanol, 2-hexanol, 5-methyl-2-hexanol, 4,6-dimethyl-2-heptanol, and cycloaliphatic alcohols.

5. The process of claim 1, in which there is included in the reaction mixture, when using barium or calcium amide, a complexing solubilizer in the form of an aliphatic tertiary amine.

6. The process of claim 5, in which the aliphatic teriary amine is N,N,N',N'-tetramethylethylenediamine.

7. In a process for the preparation of hydrocarbon solvent solutions of barium alkoxides, the steps which comprise providing a suspension of barium amide in a volatile liquid hydrocarbon or chlorinated hydrocarbon solvent, and then reacting said suspension with an alcohol selected from the group of 2-methyl-1-pentanol and 2-ethyl-1-hexanol, and removing ammonia which forms during the reaction.

8. The process of claim 7, in which there is included in the reaction mixture N,N,N',N'-tetramethylethylenediamine.

9. A process for the preparation of hydrocarbon or chlorinated hydrocarbon solvent solutions of calcium, strontium and barium 2-alkoxyalkoxides, which comprises contacting the corresponding metal lower dialkoxides of the formula $M(OR)_2$ in which R is a $C_1$–$C_3$ hydrocarbyl group, with at least two molar equivalents of a 2-alkoxy-substituted-1-alkanol, $ROCH_2CHR'OH$, where R is a $C_1$–$C_{12}$ hydrocarbyl group and R' is hydrogen or $C_1$–$C_3$ hydrocarbyl group,, and M is a metal of the group of calcium, strontium and barium, in the presence of a liquid volatile hydrocarbon or chlorinated hydrocarbon solvent.

10. In a process for the preparation of hydrocarbon or chlorinated hydrocarbon solvent-soluble calcium, strontium and barium alkoxides, the steps which comprise reacting a suspension of the corresponding metal, metal amide, $C_1$–$C_3$ metal alkoxide or dialkylmetallic compound in a volatile hydrocarbon or chlorinated hydrocarbon solvent, with a 2-alkoxy-substituted-1-alkanol ($ROCH_2CH(R')OH$), where R is a $C_1$–$C_{12}$ hydrocarbyl group and R' is a hydrogen or $C_1$–$C_3$ hydrocarbyl group; or a member of the group of γ-alkoxypoly(ethyleneoxy)-1-ethanols $RO(CH_2CH_2O)_nCH_2CH_2OH$) where R is a $C_1$–$C_{12}$ hydrocarbyl group and n is 0 to 4; or a mixture thereof with each other or with any of the alcohols of claim 1, and removing such hydrogen or ammonia as results from the reaction.

11. The process of claim 10, in which said 2-alkoxy-substituted-1-alkanols are selected from the group of 2-methoxy-1-ethanol, 2-ethoxy-1-ethanol, 2-butoxy-1-ethanol, 2-hexyloxy-1-ethanol, and 2-methoxy-1-propanol.

12. In a process for the preparation of stable hydrocarbon solvent solutions of calcium, barium and strontium organometallic compositions, the steps which comprise providing a suspension of a member of the group of metals or amides of calcium, barium and strontium or dialkylmetallic compounds thereof in a volatile liquid hydrocarbon or chlorinated hydrocarbon solvent; reacting said suspension with an alcohol as such or in solution in a volatile liquid hydrocarbon, said alcohol being selected from the group of (a) aliphatic 2-alkyl substituted $C_4$–$C_{12}$ normal monohydric alcohols, and (b) mixtures of said (a) alcohols with $C_3$–$C_{12}$ aliphatic secondary monohydric alcohols in which the hydroxyl group is attached to the second atom, removing such ammonia as forms during the reaction; and then reacting the resulting reaction product, in a liquid hydrocarbon or chlorinated hydrocarbon solvent, with at least one member selected from the group of alkyllithiums, trialkylaluminums and dialkylmagnesiums in which the alkyl radicals contain from 2 to 18 carbon atoms.

13. The process of claim 12, in which there is included in the reaction mixture a complexing solubilizer in the form of an aliphatic tertiary amine.

14. The process of claim 13, in which the aliphatic tertiary amine is N,N,N',N'-tetramethylethylenediamine.

15. The process of claim 12, in which the alkyllithiums, dialkymagnesiums and trialkylaluminums are selected from the group of n-butyllithium, sec-butyllithium, dibutylmagnesium, butyloctylmagnesium and triisobutylaluminum.

16. A chemical composition selected from the group of liquid hydrocarbon or chlorinated hydrocarbon solvent-soluble compounds of (i) calcium, strontium and barium aliphatic 2-alkyl-substituted $C_4$–$C_{12}$ primary (normal) alkoxides, and (ii) mixtures of said (i) alkoxides with calcium, strontium and barium aliphatic $C_3$–$C_{12}$ secondary alkoxides.

17. A hydrocarbon or chlorinated hydrocarbon-soluble chemical compound selected from the group of (i) barium 2-methylpentyloxide, (ii) barium 2-ethylhexyloxide, (iii) barium 4-methyl-2-pentyloxide, (iv) barium 2-ethyl-1-butoxide, (v) barium 2-ethyl-4-methyl-1-pentyloxide, and N,N,N',N'-tetramethylethylenediamine complexes thereof.

18. A composition, soluble in hydrocarbon or chlorinated hydrocarbon solvents, selected from the group of calcium, strontium and barium 2-alkoxy-1-alkoxides, $M(OCH_2CH(R')OR)_2\cdot(R''OH)_x$, in which R and R" are $C_1$–$C_{12}$ hydrocarbyl groups, R' is hydrogen or $C_1$–$C_3$ hydrocarbyl groups, M is calcium, strontium or barium, and x is 0–2.

19. A composition according to claim 18, in which the $M(OCH_2CH(R')OR)_2\cdot(R''OH)_x$ is calcium 2-ethoxyethoxide.

20. A composition, soluble in hydrocarbon or chlorinated hydrocarbon solvents selected from the group of calcium, strontium and barium γ-alkoxy-poly(ethyleneoxy)-1-ethoxides, and $M(OCH_2(OCH_2CH_2)_nOR)_2$—$(R'OH)_x$ in which R and R' are $C_1$–$C_{12}$ hydrocarbyl groups, M is calcium, strontium or barium, and x is 0–2.

21. An organometallic complex composition soluble in volatile liquid solutions of hydrocarbon or chlorinated hydrocarbon solvents comprising at least one member of the group of alkyllithiums, dialkylmagnesium and trialkylaluminums, reacted with a volatile hydrocabon or chlorinated hydrocarbon solvent solution of an alkoxide resulting from the reaction of a suspension of a metal or an amide of calcium, strontium or barium, or a dialkylmetallic compound thereof and with an alcohol as such or in solution in a volatile liquid hydrocarbon or chlorinated hydrocarbon, said alcohol being selected from the group of (a) aliphatic 2-alkyl-substituted $C_4$–$C_{12}$ monohydric primary alcohols, and (b) mixtures of said (a) alcohols with $C_3$–$C_{12}$ aliphatic secondary monohydric alcohols in which the hydroxyl group is attached to the second carbon atom, said composition being substantially free from ammonia.

22. A composition according to claim 21, in which the (a) alcohol is at least one member selected from the group of isobutyl alcohol, 2-methyl-1-pentanol, 2-ethyl-1-butanol, 2-ethyl-1-pentanol, 2-ethyl-1-hexanol, 2-ethyl-4-methyl-1-pentanol, 2-propyl-1-heptanol, 2-methyl-1-hexanol and 2-ethyl-5-methyl-1-octanol.

23. A composition according to claim 21, in which the (b) alcohol is at least one member selected from the group of isopropyl alcohol, secondary butyl alcohol, 4-methyl-2-pentanol, 2-pentanol, 2-hexanol, 5-methyl-2-hexanol, 4,6-dimethyl-2-heptanol, and cycloaliphatic alcohols.

24. A composition according to claim 21, which includes a complexing solubilizer in the form of an aliphatic tertiary amine.

25. A composition according to claim 24, in which the solubilizer is N,N,N',N'-tetramethylethylenediamine.

26. An organometallic complex composition which is soluble in hydrocarbon or chlorinated hydrocarbon solvent solutions by reaction of a member of the group of alkyllithiums, dialkylmagnesiums and trialkylaluminums with a volatile hydrocarbon or chlorinated hydrocarbon solvent solution of an alkoxide resulting from the reaction of a suspension of barium amide in a volatile liquid hydrocarbon or chlorinated hydrocarbon with an alcohol selected from the group of 2-methyl-1-pentanol and 2-ethyl-1-hexanol, said composition being substantially free from ammonia.

27. An organometallic complex composition comprising a volatile liquid hydrocarbon- or chlorinated hydrocarbon-soluble complex of (i) at least one member selected from the group of alkyllithiums, dialkylmagnesiums and trialkylaluminums in which the alkyl group or groups contain from 2 to 18 carbon atoms reacted with (ii) an alkoxide of at least one member selected from the group of calcium, strontium and barium, the alcoholic moiety of said alkoxide being at least one alcohol selected from the group of (a) aliphatic 2-alkyl substituted $C_4$–$C_{12}$ monohydric alcohols, and (b) mixtures of said (a) alcohols with $C_3$–$C_{12}$ aliphatic secondary monohydric alcohols in which the hydroxyl group is attached to the second carbon atom, said alkoxide being substantially free from ammonia, and adding N,N,N',N'-tetramethylethylenediamine.

28. A composition according to claim 27, in which the alkyl radical of said (a) alcohol contains from 4 to 8 carbon atoms.

29. A chemical compound comprising barium and calcium salts of certain alkoxides, organometallic compounds of the following groups of alkyllithium, dialkylmagnesiums and trialkylaluminums, and N,N,N',N'-tetramethylethylenediamine, selected from the group of liquid hydrocarbon- or chlorinated hydrocarbon-soluble complexes of (i) barium isobutoxide, di-n-hexylmagnesium.N,N,N',N'-tetramethylethylenediamine; (ii) barium 2-methylpentyloxide.N,N,N',N'-tetramethylethylenediamine, butylethylmagnesium and triisobutylaluminum; (iii) barium 4-methyl-2-pentyloxide, butyloctylmagnesium, triisobutylaluminum.N,N,N',N'-tetramethylethylenediamine; (iv) barium 2-methylpentyloxide.N,N,N',N'-tetramethylethylenediamine, di-n-hexylmagnesium and triisobutylaluminum; and (v) calcium isobutoxide, sec-butyllithium.N,N,N',N'-tetramethylethylenediamine.

30. A chemical compound comprising barium and calcium salts of certain alkoxides and organometallic compounds of the following groups of alkyllithiums, dialkylmagnesiums and trialkylaluminums selected from the group of liquid hydrocarbon or chlorinated hydrocarbon-soluble complexes of (i) barium 2-ethylhexyloxide and n-butylmagnesium; (ii) barium 2-ethylhexyloxide, n-butyllithium, and triisobutylaluminum; (iii) barium 2-ethylhexyloxide, butyloctylmagnesium and triisobutylaluminum; (iv) barium 2-ethylhexyloxide/4-methyl-2-pentyloxide, n-butyl-sec-butylmagnesium and triisobutylaluminum; (v) barium isobutoxide/cyclohexyloxide and n-butyl-sec-butylmagnesium; and (vi) calcium 2-ethylhexyloxide and n-butyl-sec-butylmagnesium.

* * * * *